(12) United States Patent
Abovitz et al.

(10) Patent No.: US 7,804,991 B2
(45) Date of Patent: Sep. 28, 2010

(54) APPARATUS AND METHOD FOR MEASURING ANATOMICAL OBJECTS USING COORDINATED FLUOROSCOPY

(75) Inventors: Rony A. Abovitz, Hollywood, FL (US); William F. Tapia, Longwood, FL (US); Julio J. Santos-Munne, Glenview, IL (US)

(73) Assignees: MAKO Surgical Corp., Fort Lauderdale, FL (US); Biomet Manufacturing Corp., Warsaw, IN (US)

( * ) Notice: Subject to any disclaimer, the term of this patent is extended or adjusted under 35 U.S.C. 154(b) by 0 days.

(21) Appl. No.: 12/333,599

(22) Filed: Dec. 12, 2008

(65) Prior Publication Data

US 2009/0209866 A1      Aug. 20, 2009

Related U.S. Application Data

(62) Division of application No. 11/179,909, filed on Jul. 12, 2005, now Pat. No. 7,689,014, which is a division of application No. 09/484,809, filed on Jan. 1, 2000, now abandoned.

(51) Int. Cl.
G06K 9/00      (2006.01)
A61B 5/05      (2006.01)

(52) U.S. Cl. ..................... 382/128; 600/424
(58) Field of Classification Search ................. 382/128, 382/131, 209, 219; 600/424

See application file for complete search history.

(56) References Cited

U.S. PATENT DOCUMENTS

| | | | |
|---|---|---|---|
| 4,099,880 A | 7/1978 | Kano | |
| 5,769,640 A * | 6/1998 | Jacobus et al. | 434/262 |
| 5,799,055 A | 8/1998 | Peshkin et al. | |
| 5,951,475 A | 9/1999 | Gueziec | |
| 6,011,862 A | 1/2000 | Doi et al. | |
| 6,014,452 A | 1/2000 | Zhang et al. | |
| 6,069,932 A | 5/2000 | Peshkin et al. | |
| 6,159,142 A | 12/2000 | Alt | |
| 6,477,400 B1 * | 11/2002 | Barrick | 600/426 |
| 6,532,380 B1 | 3/2003 | Close et al. | |
| 6,701,173 B2 * | 3/2004 | Nowinski et al. | 600/407 |
| 6,782,284 B1 | 8/2004 | Subramanyan et al. | |
| 7,225,011 B2 | 5/2007 | Mielekamp | |
| 7,289,652 B2 | 10/2007 | Florent et al. | |
| 7,319,905 B1 * | 1/2008 | Morgan et al. | 607/129 |
| 7,367,809 B2 * | 5/2008 | Takahashi | 434/262 |
| 7,379,062 B2 * | 5/2008 | Poole | 345/424 |
| 7,398,116 B2 * | 7/2008 | Edwards | 600/424 |
| 7,452,364 B2 * | 11/2008 | Schreiber et al. | 606/153 |
| 7,477,926 B2 * | 1/2009 | McCombs | 600/407 |
| 7,559,931 B2 * | 7/2009 | Stone | 606/91 |
| 7,580,554 B2 * | 8/2009 | Spahn | 382/128 |
| 7,630,750 B2 * | 12/2009 | Liang et al. | 600/407 |

(Continued)

*Primary Examiner*—Bhavesh M Mehta
*Assistant Examiner*—Mia M Thomas
(74) *Attorney, Agent, or Firm*—Fay Sharpe LLP (57) ABSTRACT

Two fluoroscopic images taken from two different angles of the same anatomical feature are registered to a common three-dimensional coordinate system. A dimension of the anatomical feature is determined by specifying with reference to the two registered fluoroscopic images two constrained points within the three-dimensional coordinate system that correspond to the boundaries of the anatomical feature, and calculating a straight-line distance between the two. Additionally, a three-dimensional virtual model of an implant is projected into each of two, registered fluoroscopic image, and a surgeon manipulates the projections to adjust the size and shape of the virtual model, and thereby determine parameters for the implant.

6 Claims, 9 Drawing Sheets

U.S. PATENT DOCUMENTS

| | | |
|---|---|---|
| 2001/0021806 A1 | 9/2001 | Gueziec et al. |
| 2002/0049378 A1* | 4/2002 | Grzeszczuk et al. ......... 600/427 |
| 2002/0082492 A1* | 6/2002 | Grzeszczuk ................. 600/407 |
| 2003/0076987 A1* | 4/2003 | Wilson et al. ............... 382/128 |
| 2003/0210820 A1* | 11/2003 | Lachner et al. ............. 382/209 |
| 2004/0015070 A1 | 1/2004 | Liang et al. |
| 2004/0171922 A1 | 9/2004 | Rouet et al. |
| 2005/0004454 A1* | 1/2005 | Mitschke et al. ............ 600/427 |
| 2005/0053267 A1 | 3/2005 | Mostafavi |
| 2005/0288578 A1* | 12/2005 | Durlak ....................... 600/434 |
| 2006/0025681 A1 | 2/2006 | Abovitz et al. |
| 2006/0039591 A1 | 2/2006 | Zettel et al. |
| 2006/0251300 A1 | 11/2006 | Borgert et al. |
| 2007/0092142 A1* | 4/2007 | Kuriathungal et al. ...... 382/209 |
| 2007/0211927 A1 | 9/2007 | Groszmann et al. |
| 2008/0101667 A1 | 5/2008 | Begelman et al. |
| 2008/0132774 A1 | 6/2008 | Milstein et al. |
| 2008/0144914 A1* | 6/2008 | Wagner et al. .............. 382/132 |
| 2009/0088830 A1* | 4/2009 | Mohamed et al. .......... 623/1.11 |
| 2010/0063420 A1* | 3/2010 | Mahn et al. ................. 600/594 |
| 2010/0121181 A1* | 5/2010 | Wang et al. ................. 600/424 |

* cited by examiner

APPARATUS AND METHOD FOR MEASURING ANATOMICAL OBJECTS USING COORDINATED FLUOROSCOPY

This application is a divisional application of U.S. application Ser. No. 11/179,099, filed Jul. 12, 2005, which is in turn a divisional application of U.S. application Ser. No. 09/484,809, filed Jan. 1, 2000.

FIELD OF THE INVENTION

The present invention relates to an apparatus and method for measuring anatomical objects in the body and/or to sizing surgical implant or devices.

BACKGROUND OF THE INVENTION

Measuring anatomical features might be expected to be done on a three-dimensional data set, such as can be reconstructed from data taken during a computed tomography (CT) scan or a magnetic resonance image (MRI) scan. However, equipment for CT and MRI scans are expensive and bulky. Furthermore, they may not be available when and where needed. For example, CT and MRI equipment is usually not available for use during a medical intervention procedure, or within an operating room or treatment area.

Where knowledge of the anatomical feature is very important, a CT or MRI scan might be taken in advance of the procedure and the procedure planned based on it. However, there are many more medical procedures and interventions that might benefit from knowledge of the size of an anatomical feature in the patient, where the cost a CT scan is not justified or CT equipment is not available. For example, to treat a tumor or aneurysm, it is often helpful to know the size of the tumor or occlusion. Similarly, it would be helpful to know in advance of surgical interventions that involve implanting stents, screws, nails, or other devices in the body how well a chosen device will fit, or if a device of a different size or shape would be more appropriate.

SUMMARY OF THE INVENTION

Unlike CT and MRI scans, fluoroscopic images are easily acquired and, as compared to CT and MRI scans, relatively inexpensive. The equipment can be located, if necessary, in a surgery or treatment room, and can be used during course of an intervention if necessary. A physician or surgeon also has control over the positioning of the fluoroscope relative to the patient, thereby allowing the doctor to take the images the doctor prefers. With an accurate knowledge of an anatomical dimension, the chance for success of a medical or surgical procedure will often be improved. For example, determining accurately an anatomical dimension with a fluoroscope can assist with the selection of the correct size of implantable device, or with the preparation of a custom-made device, without having to use CT or MRI scans.

In accordance with one objective, one embodiment of the invention determines the distance between two or more anatomical landmarks. At least a first and a second fluoroscopic image are taken from different—though not necessarily orthogonal—angles of the same portion of a patient's body. These images are registered using a computer to a common three-dimensional coordinate system of the workspace or patient. A user specifies to the computer at least two points within the first fluoroscopic image corresponding to anatomical landmarks within the first image that are identified by the user. Each of the two points specified in the first image defines, in accordance with a predetermined geometric model of the fluoroscope, an imaginary "line of sight" in the three-dimensional coordinate system that can be indicated on the second image. The user indicates to the computer, with reference to the second image, where along each imaginary line of sight the corresponding anatomical landmark lies. Additional points in the three-dimensional coordinate system that correspond to other anatomical landmarks may also be specified by the user should the user be interested in determining a length of a curved line passing through (or near to) them. The computer then determines, based on the positions within the three-dimensional coordinate system of the specified points, the length of the line specified by them. In the case of two points, this length would be the straight line and thus represent the shortest distance between the two points. Using two points would be useful for finding a dimension of an anatomical object, for example the diameter of a blood vessel. If the case of three or more points being specified, this length would be of the line, straight or curved, passing through the points. For example, finding the length of a curved object, such as a portion of a blood vessel, could be reasonably accurately determined by specifying a plurality of points that indicated approximately the centerline of the object. The length of a contour of an anatomical object could be determined in a similar manner.

In accordance with another object, the rate of velocity and the rate of acceleration of an object within the body is determined by identifying the position of the object in successive, fluoroscopic images registered to a common frame, taken at known time intervals. For example, a leading edge or crest of a boundary of radio-opaque dye injected into a blood vessel is used as a marker to determine volumetric blood flow rate.

In accordance with another objective, another aspect of the preferred embodiment of the invention includes a definition of a three-dimensional "virtual surgical object." The virtual surgical object has one or more attributes corresponding to one more physical characteristics of a surgical object to be implanted in the patient, for example the shape and size of the outer surface of the surgical object. The computer displays a two-dimensional graphical representation of this virtual surgical object, referred to as a "projected surgical object," on each of two or more fluoroscopic images registered to a common, three-dimensional coordinate system. A user identifies at least an initial location for the virtual surgical object within the patient, such as by identifying a point in one of the images at which its projected surgical object is to be drawn in that image. Once an initial position of the virtual surgical object is defined, the computer then draws corresponding projected surgical objects in all of the images. Because each projected surgical object is constrained to correspond geometrically to the same virtual surgical object in three-dimensional space, manipulation through a user input of a projected surgical object will cause a change in positioning, size and/or orientation in the virtual surgical object, and thus result in the computer redrawing the projected surgical object(s) in the other image(s) to correspond to the change. The user is thereby able to manipulate the virtual surgical object and determine its fit with the anatomy of the patient based on the alignment of the projected surgical objects with the anatomical feature shown in each of the images. If necessary, the user can try a different predefined virtual surgical object, or resize or reshape the virtual surgical object by altering one or more attributes of the virtual surgical object. The user may alter the attributes through revising the definition of the virtual surgical object and/or through manipulation of one or more of the graphical representation constituting the projected surgical objects. Once the appropriate size and/or shape of the virtual surgical object is determined, the information can be used to select the most appropriate prefabricated implantable surgical object, to custom make an implantable surgical object, to determine the fatigue (e.g., maximum stresses and strains) life of the implantable surgical object, to determine whether an implantable surgical object will not function properly once implanted (e.g., the kinking of a stent graft in torturous vessel), or to customize an existing surgical object.

The forgoing is a summary of various aspects of disclosed embodiments of the invention, as well as of the advantages offered by these aspects. It is not intended to limit the scope of the invention as defined in the appended claims. These and other features and advantages of the disclosed embodiments are next described in detail, with reference to the appended drawings, in which:

DETAILED DESCRIPTION OF DRAWINGS

In the following description, like reference numbers refer to like parts.

Figure 1:
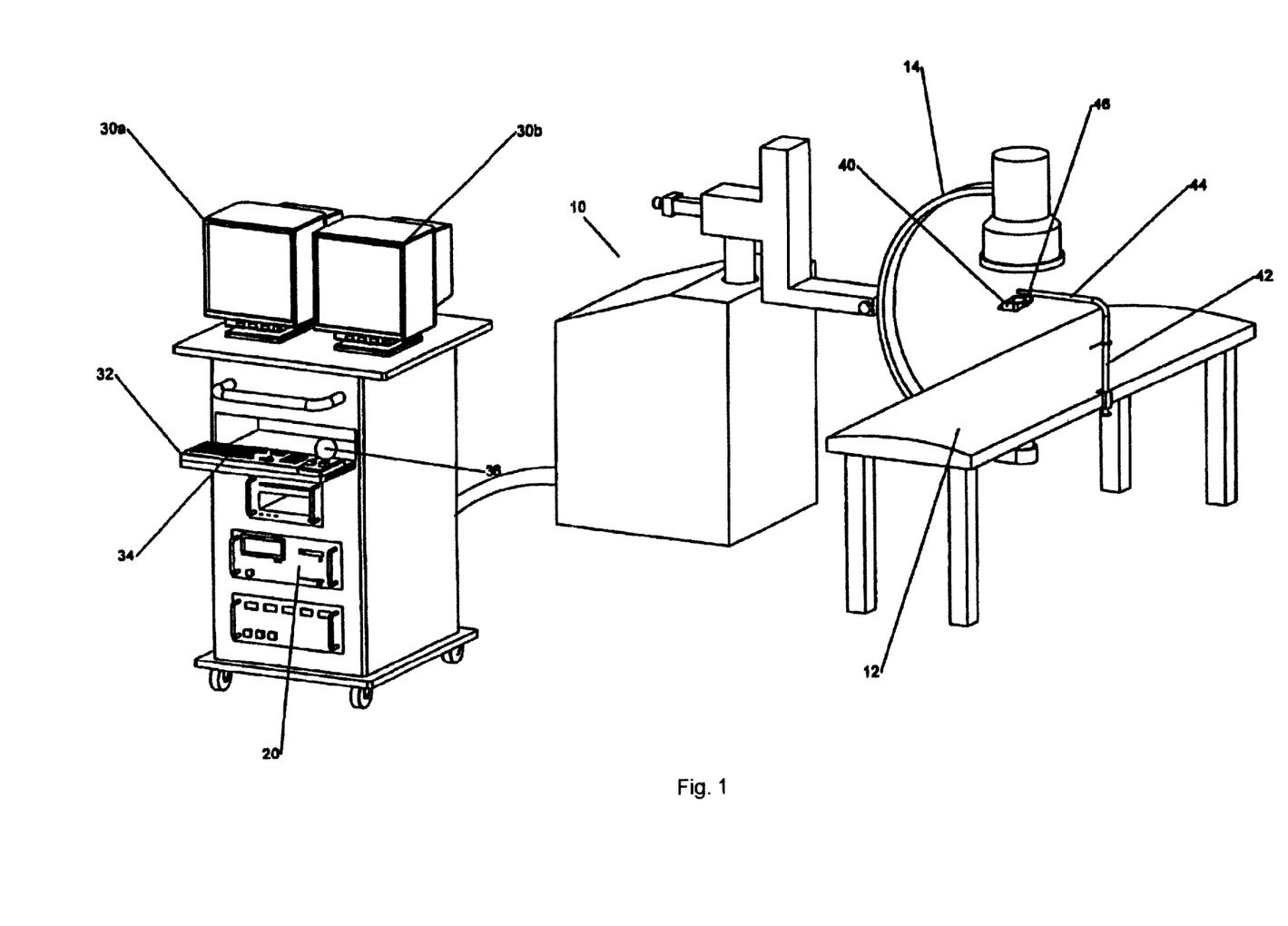
FIG. 1 is a diagrammatic illustration of a fluoroscope and programmed computer for use in stereotactic measurement of anatomical objects.

Referring to FIG. 1, C-arm type fluoroscope 10 generates fluoroscopic or x-ray images of a body on a surgical table 12. Imaging arm 14 of the fluoroscope 10 can be slid on its mounting base so that it can be rotated around the table to enable images to be taken from different angles and thereby obtain different poses. The C-arm fluoroscope is a representative example of fluoroscopes typically used in hospital operating rooms. The invention can be used, however, with other types of fluoroscopes. A fluoroscope illuminates a target body with electromagnetic radiation at X-ray wavelengths and sensing or recording the resulting shadow using a camera or film sensitive to the radiation. The fluoroscope can be used for either intermittent image capture or continuous video. However, continuous fluoroscopy during a surgical procedure is undesirable because it exposes the surgeon and patient to excessive radiation. Thus, typically, fluoroscopic images are taken of a patient immediately before or during surgery to assist the surgeon in planning the operation. As exemplified by the C-arm fluoroscope 10, a fluoroscope is easily positioned in any number of arbitrary positions around the patient as compared to other types of medical imaging equipment. Furthermore, as compared to more advanced forms of imaging such as computed tomography (CT), fluoroscopy is relatively inexpensive.

Figure 2:
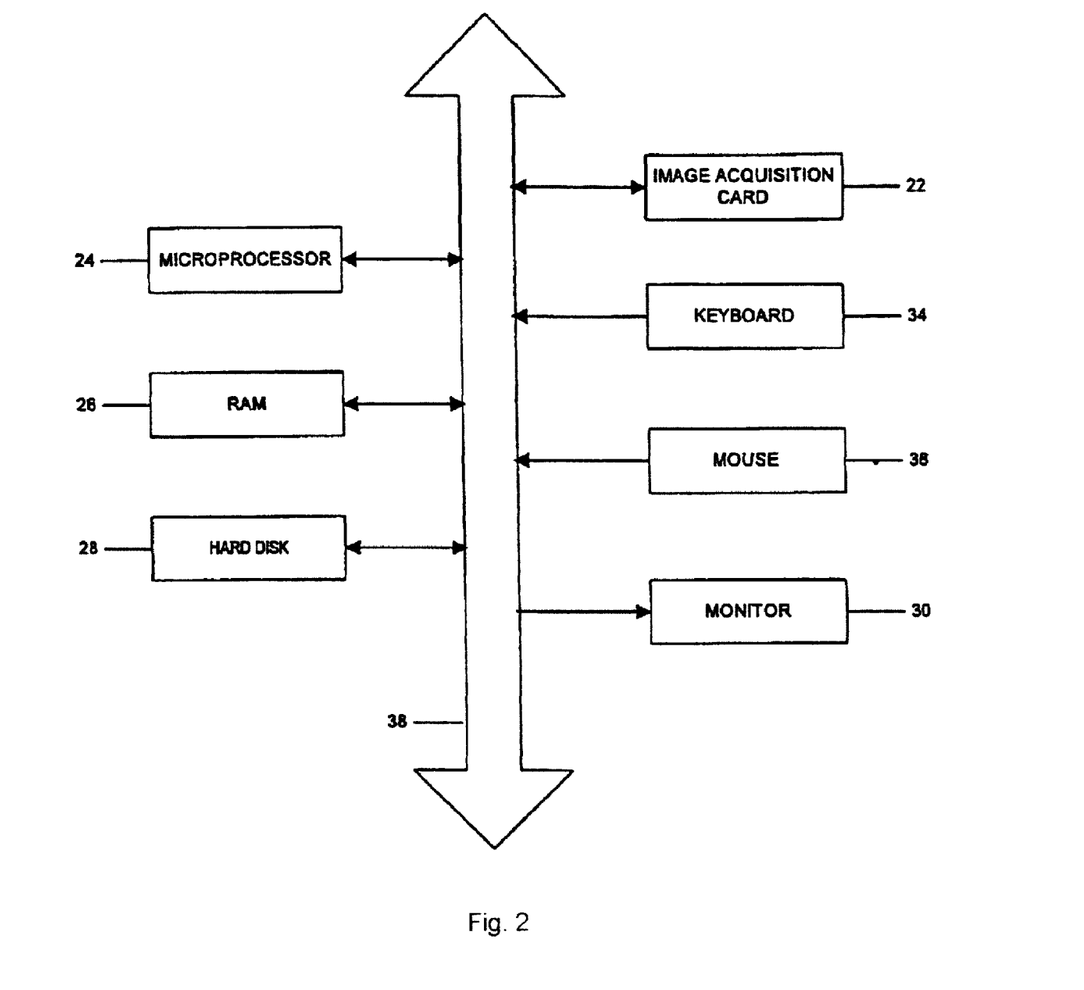
FIG. 2 is a schematic representation of a computer.

Referring briefly to FIG. 1 and FIG. 2, computer 20 is a device, such as a programmable workstation or desktop computer, capable of executing certain processes described below in connection with FIGS. 4-9. Programmable desktop computers suitable for executing the processes include personal computers, networked workstations and graphical workstations. FIG. 2 is a schematic representation of basic functional components typically found in a programmable, general-purpose computer. The computer is coupled to fluoroscope 10 for receiving fluoroscopic images through an image acquisition card 22. The computer includes a microprocessor 24 for running software instructions, random access memory (RAM) 26 for temporarily storing software instructions and data during execution of programs, and a hard disk drive 28 for non-volatile storage of data, program and other types of files. Computer 20 is also coupled to at least one graphics monitor 30. The graphics monitor 30 is used to display fluoroscopic images as well as to provide a user interface for the exchange of information and commands between processes running on the computer and the user. Two monitors are actually shown in FIG. 1: monitor 30a displays an A/P image and monitor 30b displays sagittal image. However, a single monitor can be used to display two or more images in multiple windows or by switching between the images. The following description will be in reference to a computer with a single monitor 30 (FIG. 2). Computer 20 is also coupled to a user input device 32. In the illustration, the input device includes several components: a keyboard 34 for entering typed commands and information; and a track ball or mouse 36 for moving a cursor or pointer on the monitor. The various components within the computer communicate with each other over a bus structure, which is conceptually represented by bus 38.

Figure 3:
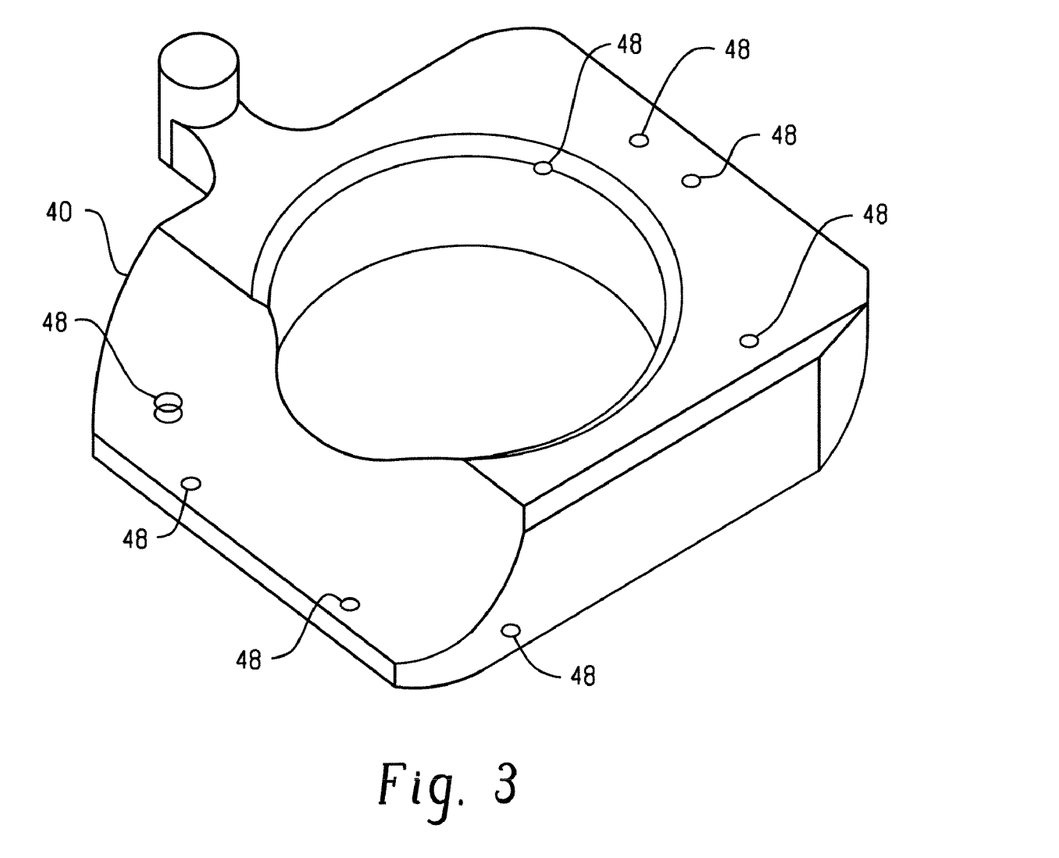
FIG. 3 illustrates a registration artifact.

Referring now to FIGS. 1 and 3, fluoroscopic images taken from different poses or angles must be registered to a common three-dimensional frame or coordinate system, in which the patient is in a fixed position. Registration involves determining a correspondence between each fluoroscopic image and the workspace in which the patient lies. Several methods can be used to register the images. Typically, registration has been derived from positioning of the fluoroscope. However, the preferred registration method is described in U.S. Pat. No. 5,799,055 of Peshkin and Santos-Munne, which is incorporated herein by reference for all purposes. According to this method, a registration artifact 40 that is held in a fixed position relative to the patient while one or more fluoroscopic images are acquired from different angles or "poses" using fluoroscope 10. The registration artifact is positioned using a flexible arm 42 situated adjacent the surgical table 12. Flexible arm 42 includes a flexible arm assembly 44 having an end flange 46. The registration artifact 40 is coupled to the end flange 46. The flexible arm 42 can adjust the position of artifact 40 in three-dimensions.

The Peshkin-Santos-Munne registration method does not depend on knowledge of the positioning of the fluoroscope. Rather registration is determined from the fluoroscopic images. The registration artifact 40 is X-ray transparent with the exception of a plurality of radio-opaque spheres or fiducials 48. In the illustrated artifact there are eight fiducials. The fiducials 48 are easily identifiable on a fluoroscopic image. The positions of these fiducials relative to a three-dimensional coordinate system are fixed by the artifact, and are known either by design or by measurement. The artifact is shaped so that none of the fiducials will cast a shadow, or block, any of the other fiducials when roughly orthogonal images are taken. From the two-dimensional locations of the projections of these fiducials in a fluoroscopic image, which are small, well-defined dots, geometric projections that carry a three-dimensional point anywhere in the vicinity of the artifact into a projected point on the image can be determined. This establishes registration between image and workspace. Several images can each be registered relative to the same registration artifact, thus also bringing all the images into registry with one another. The method disclosed by Peshkin and Santos-Munne thus enables the determination of projective geometric relationships that relate each of two or more acquired fluoroscopic images to the three-dimensional workspace around and within the patient's body, despite essentially arbitrary positioning of the fluoroscope. There is no requirement that the poses be orthogonal, nor is there a need to instrument the fluoroscope so that the pose angles can be measured.

According to the registration method described in detail in U.S. Pat. No. 5,799,055, the two-dimensional coordinates of the fiducials within an image are determined. The image is then registered by projecting the known three-dimensional coordinates of the fiducials into the two-dimensional image points of the fiducials according to a predetermined geometric model, and then numerically optimizing the parameters of the geometric model such that the projections of the known three-dimensional coordinates of the fiducials best fit the identified two-dimensional coordinates in the image. This method is repeated for all images taken of the patient's body and the registration artifact but from an angle different from that of the first image. Thus, a transformation and its inverse are obtained for mapping between a point defined within the two-dimensional image to a line in the three-dimensional coordinate system. A mathematical description of the numerical optimization of the model and the mapping can be found in the Appendix to U.S. Pat. No. 5,799,055.

Figure 4:
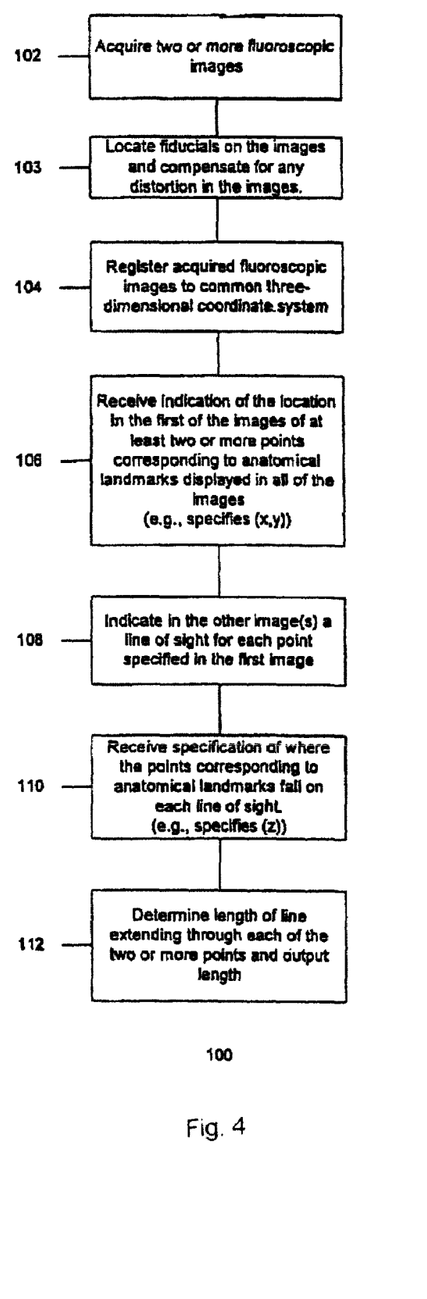
FIG. 4 is a flow chart of the basic steps of a method for measuring, using two or more fluoroscopic images, a distance of a line defined by two or more points corresponding to anatomical landmarks identified by a user.

Referring now to FIG. 4, illustrated is a method 100 for measuring an anatomical feature using the system of FIG. 1 by specifying two or more anatomical landmarks. The method will be described in reference to FIG. 1, as well as to FIGS. 5 and 6. At step 102, a user, such as doctor, nurse or technician, acquires two or more fluoroscopic images from different angles or poses of a portion of a patient lying on table 12 (FIG. 1). For example, for purposes of this description, the acquired images are taken from an anterior/posterior (A/P) pose and a sagittal pose. The images are displayed on monitors 30a and 30b, respectively. The images are then registered at step 104 to a known three-dimensional coordinate system in which the patient is located. Alternately, one image at a time can be acquired and registered. In this case, steps 102 and 104 would be repeated for each image.

Figure 5:
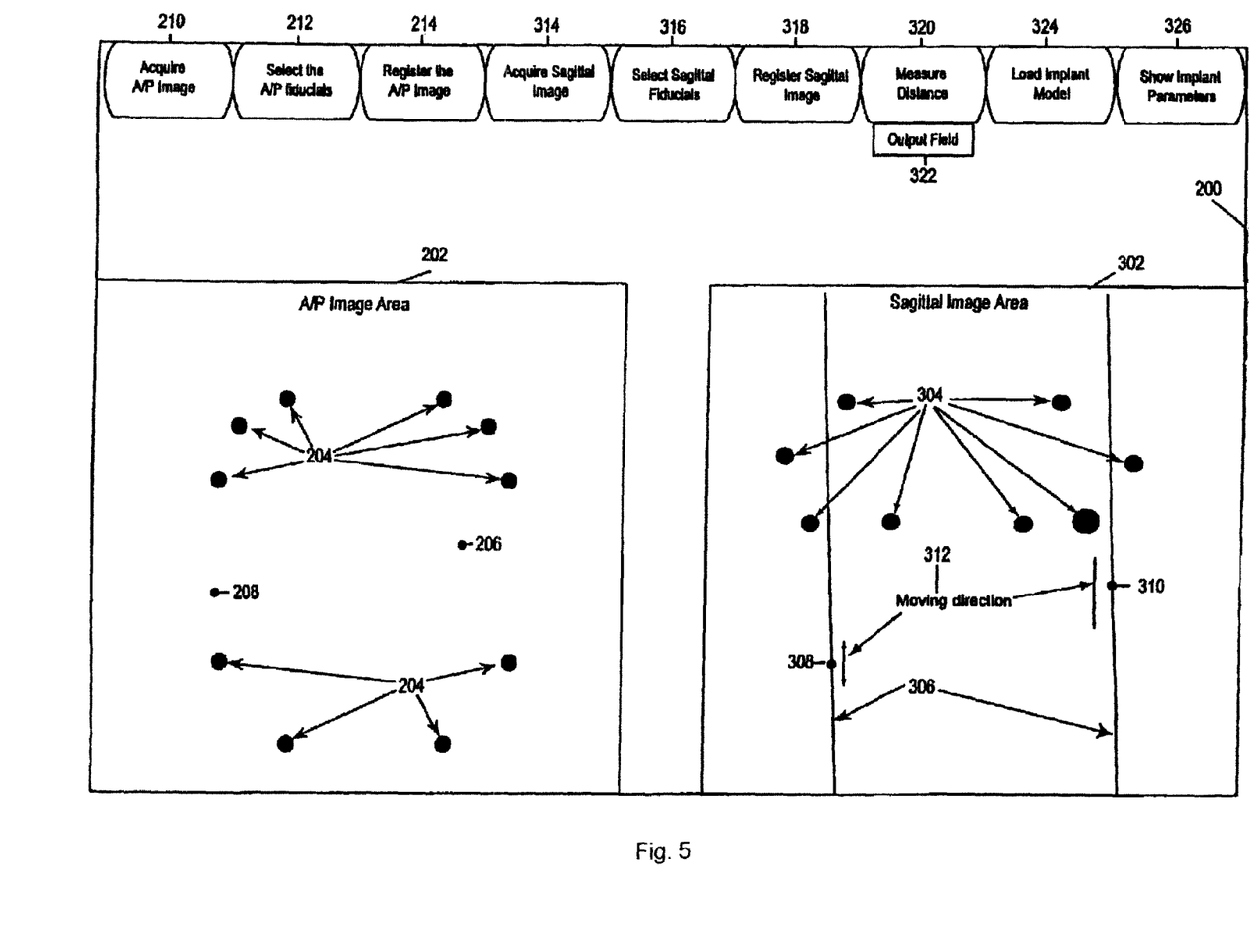
FIG. 5 is a sample screen display of the computer in FIG. 1 displaying an anterior/posterior (A/P) image taken by the fluoroscope of FIG. 1 of a patient.

As previously stated, the registration method of U.S. Pat. No. 5,799,055 is the preferred method of registration. Other methods could be used, but without the benefits of this method. FIG. 5 illustrates the appearance of a screen 200 of the monitor when displaying an A/P image 202. For purposes of clarity, outlines of anatomical features have been left out of the image. The image contains a plurality of dots 204 that are shadows of fiducials 48 of the registration artifact 40 (FIG. 3). Similarly, screen 300 of FIG. 6 displays the sagittal image 302 containing a plurality of dots 304 that are shadows of the same fiducials. For accurate registration, all of the fiducials 48 in the registration artifact 40 should appear in each image. If not, the artifact 40 or the imaging arm 14 is adjusted so that all eight fiducials appear.

To register an image, the location of each fiducial's shadow within an image is identified. This location is specified using a two-dimensional coordinate referenced to the image. This can be done by the user pointing to the shadow with a cursor or other pointing device, or by the computer intelligently determining fiducials' shadows by their shape and relative positions using a pattern recognition algorithm. Once the locations of the shadows of all the fiducials are identified within an image, the computer registers the image through methods described in U.S. Pat. No. 5,799,055. In connection with the registration, the computer will account for distortion in the images caused by the fluoroscope's image intensifier, as described in U.S. Pat. No. 5,799,055. For example, such distortion will cause a straight line in the three-dimensional workspace of the patient to appear curved in the image. To account for this distortion, the computer may correct the distortion in the displayed images. Alternately, to avoid the processing associated with correcting each image, the computer may correct for the distortion when mapping between a two-dimensional coordinate point in an uncorrected image and the three-dimensional coordinate system. Although not necessary for the method of FIG. 4, or the method of FIG. 7 to be discussed next, correcting the images is advantageous, especially for the method of FIG. 7 and FIG. 8. The images 202 and 302 of FIG. 5 are corrected.

Once the images have been registered, the process of FIG. 4 continues at step 106 with the user specifying to the computer the location within one of the two images, in the case the A/P image 202 (FIG. 5), two or more points corresponding, respectively, to two or more anatomical landmarks. If a distance between two anatomical landmarks is desired, only two points need to be specified. For example, should a surgeon desire to know the precise diameter of a tumor at a particular location, points on diametrically opposite sides of the tumor are specified. Should a user be seeking the length of a curved or non-linear surface or other anatomical feature, several points can be specified along its length. For example, should a surgeon desire to determine the length of an artery that is not straight, the centerline of the artery can be specified with a plurality of points spaced along its length that approximates it.

For purposes of this description, a user has specified two points, represented graphically by points 206 and 208 drawn on the A/P image 202 of FIG. 5, by positioning a cursor or using some other type of pointing mechanism device to identify two anatomical landmarks and signaling the computer (e.g. by clicking a mouse button) to accept the coordinates of the pointing mechanism as specifying the points to be used in measuring an anatomical distance or dimension. The computer then draws or displays within the image 202 on the computer screen a dot superimposed on each anatomical landmark specified by the user. By specifying these two points in the A/P image, the user has specified, in effect, a line of sight within the three-dimensional space of the patient that can be uniquely identified within the three-dimensional coordinate system to which the image has been registered. This line of sight is determined by the transformation mentioned above that maps each point within the two-dimensional image to the three-dimensional coordinate system.

Proceeding to steps 108 and 110 of FIG. 4, to reduce each line of sight to a point in the three-dimensional workspace of the patient, the user specifies to the computer the positions of the anatomical landmarks in the other image, in this example the sagittal image 302 of FIG. 5. The computer, however, constrains the user to specifying or selecting points that lie along each line of sight. To assist the user, the lines of sight for the points specified on the A/P image 202 are represented by lines 306 drawn by the computer on the image 302. Furthermore, if desired, the computer may specify within the three-dimensional coordinate system default locations of the points and draw corresponding projections as dots 308 and 310. Once the dots are displayed, the user is able to slide them, using a mouse or other pointing device, along the lines as indicated by arrows 312 until they align with the respective anatomical landmarks.

At step 112 of FIG. 4, once two points in the three-dimensional workspace are defined, the computer calculates the straight line distance between them and provides it for use by the user, such as on the computer screen 200 or to some other device. Should more than two points be specified, the computer best fits, using well known techniques, a curve to the points that terminates at the points most distant from each other. If desired, the user could specify the type of curve. The length of the curve is then calculated, and the result provided to the user or other device.

Referring now to only FIG. 5, the screen 200 preferably includes a graphical user interface. The graphical user interface features software buttons, and/or drop-down menus, that can be pushed to change the mode of operation or to perform some predefined function or process. Preferably, the buttons are located on the screen outside the area in which the fluoroscopic images are displayed. The menus and buttons can be made context sensitive. For example, in FIG. 5, selecting button 210 signals the computer to commence the process of acquiring an A/P image from the fluoroscope, button 212 starts a process for selecting or identifying the fiducials within the image for registration, and button 214 starts a process for calculating the registration of the image to a three-dimensional coordinate system. Selecting button 314 starts the process of acquiring a sagittal image, button 316 starts the process of identifying the fiducials and button 318 starts the process of calculating the registration of the image. FIG. 5 also includes a button 320 for initiating the measurement process of step 112 (FIG. 4) between the specified points and a display area 322 for displaying the resulting measurement. Also illustrated are two buttons whose use will be described in connection with an alternate process for determining an appropriate size or shape for an implant illustrated by FIGS. 6 and 7: button 324 starts a process for loading a predefined virtual surgical object and button 326 starts a process for providing, by display or otherwise, parameters of the virtual surgical object.

Figure 6:
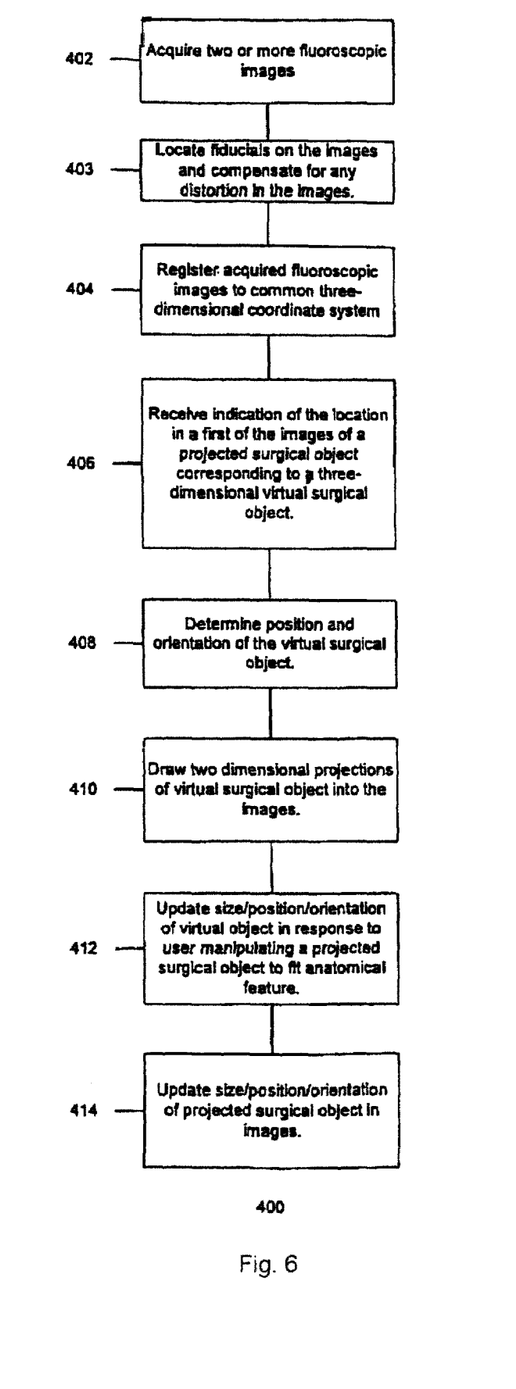
FIG. 6 is a second sample screen display of the computer in FIG. 1 showing in place of the A/P image of FIG. 5 a sagittal image of a patient taken by the fluoroscope of FIG. 1.
Figure 7:
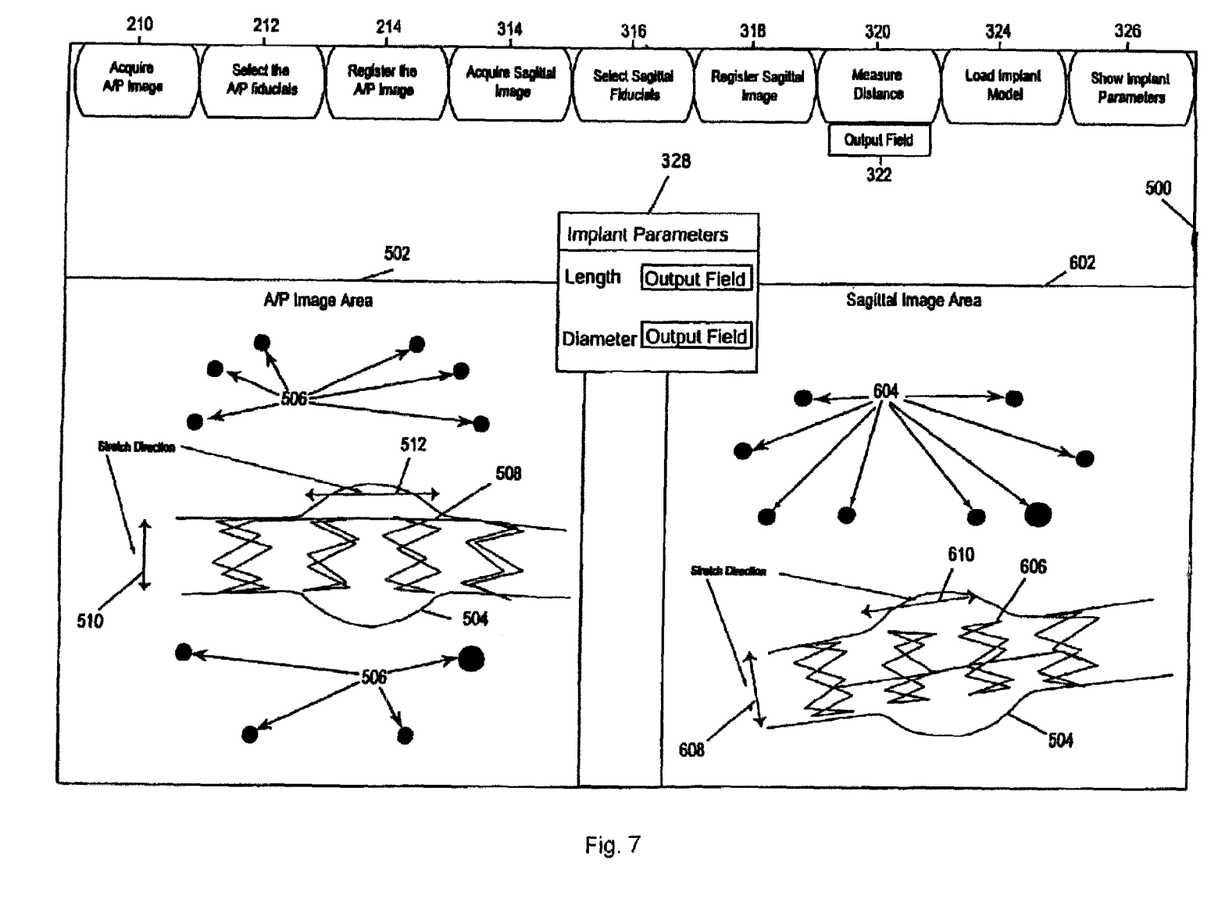
FIG. 7 is a flow chart of the basic steps of a computer a method for use in determining the fit of a surgical implant in advance of implantation using two or more fluoroscopic images.

Referring now to FIGS. 6 and 7, method 400 of FIG. 6 describes a computer-aided process by which fluoroscopic images may be used to assist with selecting or defining a size and shape of a surgical object to be implanted in a patient. This process can be used in conjunction with, or as an alternate to, the method 100 described in connection with FIGS. 4 and 5. For example, method 100 (FIG. 4) can be used to make an initial selection of an implant, and the method 400 used to test and/or refine the selection.

Process 400 starts with steps 402, 403 and 404, in which two or, optionally, more fluoroscopic images are acquired and registered to a common three-dimensional coordinate system. These steps are substantially the same as steps 102, 103 and 104 of FIG. 4. FIG. 7 is an illustration of a screen 500 generated by computer 20 (FIG. 1). It displays an A/P image 502 and sagittal image 602 acquired during step 402. The A/P image includes a picture of an artery 504 of a patient taken from an A/P pose. Dots 506 correspond to the fiducials 48 in the registration artifact 40. The sagittal image includes a picture of the artery 504 in a sagittal pose. Dots 604 correspond to the fiducials in registration artifact 40.

At step 406, a user specifies to the computer by reference to either of the images, but in this example, to image 502, the location of a virtual surgical object or implant model. A virtual surgical object is a three-dimensional model of an object to be implanted into a patient. The model is defined within the three-dimensional coordinate system to which the images are registered. In this example, a user specifies a point in image 502, and then switches to image 602 to designate a point along the line of sight defined by the selection of the point on image 502 at which the virtual surgical object will be loaded. This then defines a point in the three-dimensional coordinate system at which a virtual surgical object will be located, the coordinates for which the computer determines at step 408. These steps are not illustrated by FIG. 7.

At step 410 of process 400 (FIG. 6), the user pushes button 324 to load a predefined virtual surgical object at the designated point. The computer then draws on the images 502 and 602 a two-dimensional graphical representation of the virtual surgical object projected onto the images according to the predetermined geometrical model with which the images have been registered to the three-dimensional coordinate system or workspace. This graphical representation will be referred to as a projected surgical object. In the illustrated example, the surgical object is a stent that will be inserted into artery 504. The three-dimensional model of the stent that serves as the virtual surgical object in this example is a tube having a length and outer diameter that can be specified by the user or be set to correspond to a stent of some standard size. In FIG. 7 the projected surgical object is projected stent 508, and in FIG. 9 it is projected stent 606. The illustrations show both projected stents to be within artery 504. However, a surgeon may want to test different sizes and/or shapes to determine the most appropriate stent for implanting in the patient.

At step 412, in order to determine the best fit of a surgical object with the anatomy of a patient, the user can manipulate or alter the graphical features of either projected surgical objects in order to change the size, shape or orientation of the virtual surgical object. The user manipulates the projected surgical object with a pointing device or by entering some numerical value indicating a change in the projected surgical object. The computer then, in response to this manipulation, recalculates the position, size and/or orientation of the virtual surgical object and updates at step 414 the projected surgical objects on each image so that they remain accurate projections of the virtual surgical object. Alternately, or in addition to the manipulation of the projected surgical object, the user may manipulate the virtual surgical object by entering directly a change in one or more of the parameters of the model for the virtual surgical object. The projected surgical objects on the fluoroscopic images 502 and 602 are thus constrained by the virtual surgical object: a change in one of the projected surgical objects results in change in the other projected surgical objects. Once the user is satisfied with the fit, the computer provides the parameters of the model to the user or to some other device if desired. In the disclosed embodiment, a software button 326 (FIG. 7) is provided to cause the computer to provide or display on the screen the parameters of the virtual surgical object 328 (FIG. 7). With these parameters, an appropriate surgical object or implant may be fabricated or, alternately, selected and, if necessary, modified for insertion.

In the illustrated example, the outline of the exterior surfaces of the virtual stent can be manipulated by the user stretching the apparent diameter of projected stent 508, as indicated by arrow 510 and arrow 608 in FIG. 7, or its length, as indicated by arrow 512 and arrow 610 in FIG. 7. To stretch the projected stents, the user manipulates, in preferred embodiment, the projected stents with a pointing device, such as a mouse or trackball that controls a position of a cursor. A pointing device is more intuitive for a user when trying to obtain the best fit between a projected surgical object and an anatomical feature. Other types of pointing devices could be used, such as a touch screen. However, numerical values can be entered instead to specify the amount of stretch.

More complex models of a virtual surgical object could allow for reshaping, bending or other manipulation, such as might be done to alter the object prior to, or during, implantation. These models could, furthermore, be programmed to alert the surgeon as to possible failures due to the manipulation or limit the user to permitted alterations. For example, in the case of stent, the model may allow the tubular-shaped stent to be bent to conform to the shape of an artery, such as might be done during surgery. However, bending the stent too far may cause the wall of the stent to collapse or kink, thereby reducing the cross-sectional flow area of the stent and thereby defeating its purpose. The model could therefore either warn of problem with a message, refuse to be manipulated in the fashion desired by the user, or simply illustrate the resulting problem—the kink in the forgoing example.

Figure 8:
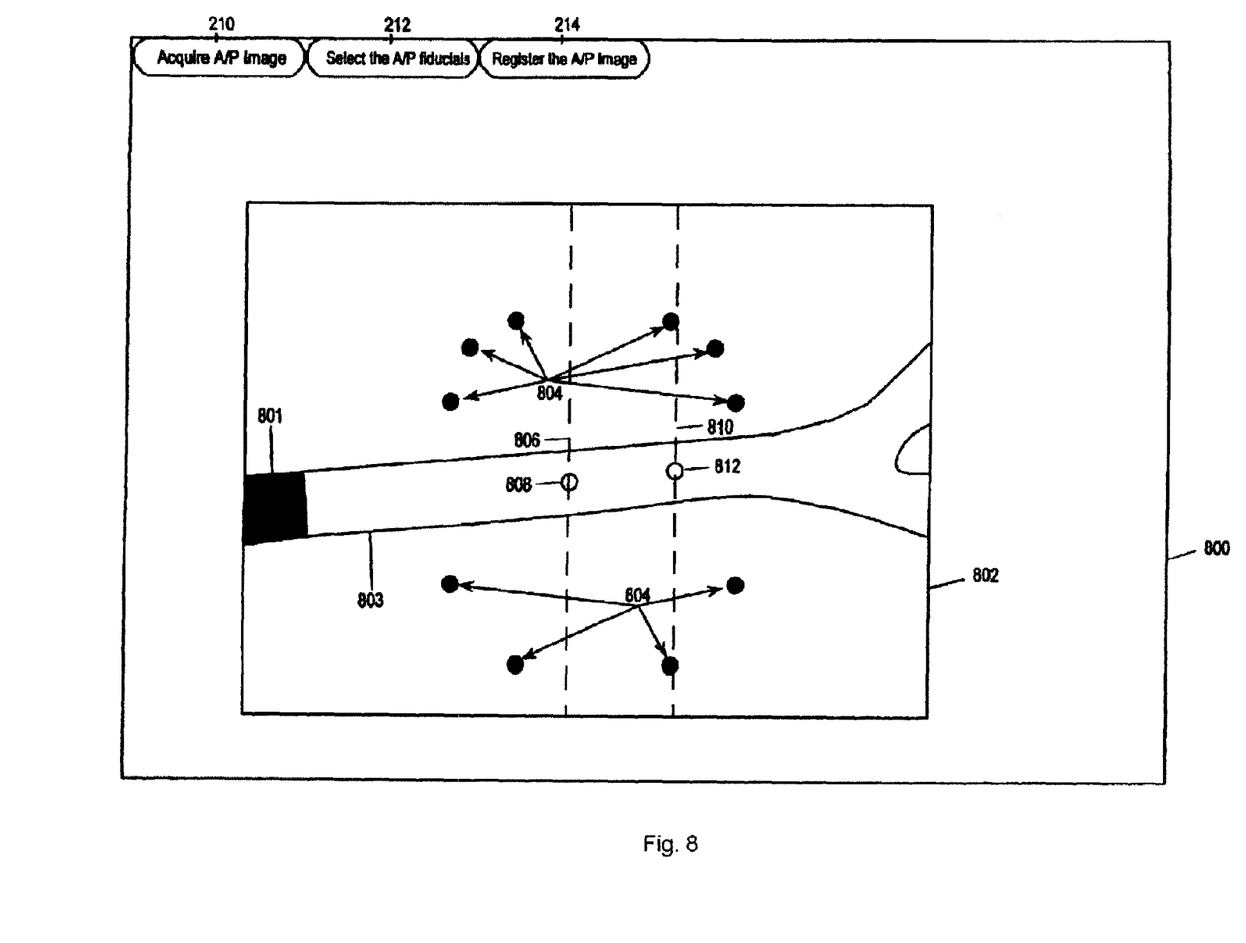
FIG. 8 is a sample screen display from the computer of FIG. 1 showing a first image of a blood vessel injected with radio opaque dye, taken from a first pose.
Figure 9:
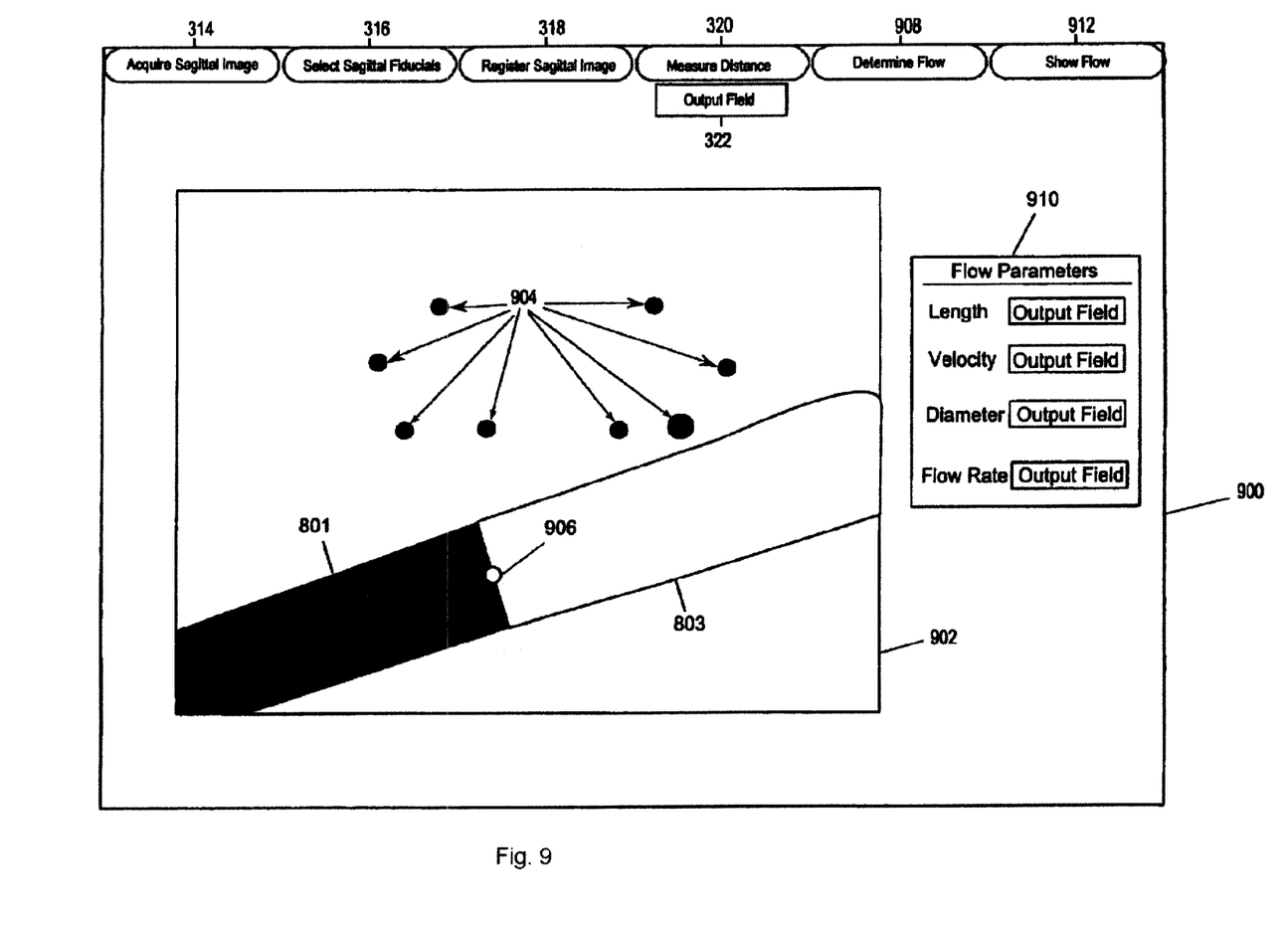
FIG. 9 is a sample screen display from the computer of FIG. 1 showing a second image of the blood vessel, but taken from a second pose and at a time subsequent to the first image, showing progression of the dye within the blood vessel.
Figure 10:
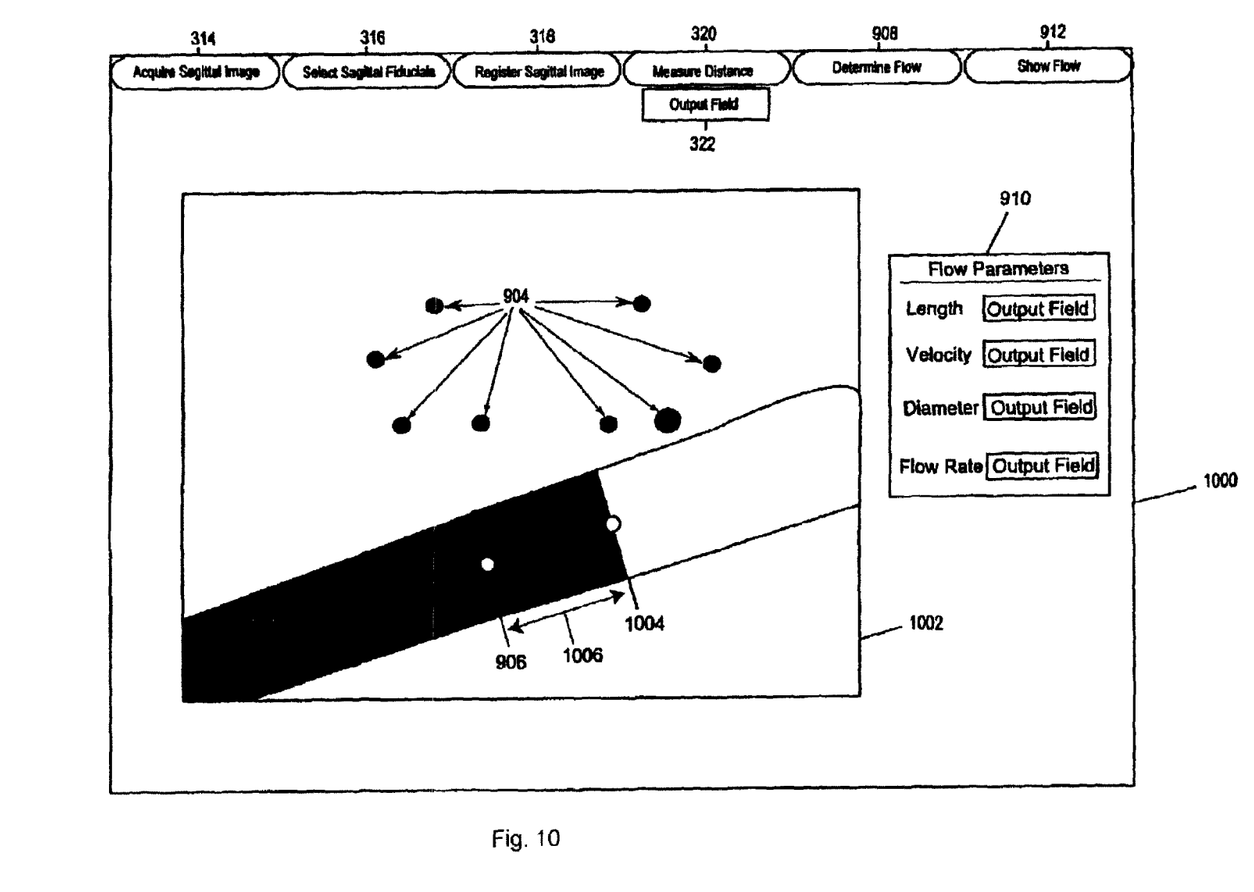
FIG. 10 is a sample screen display showing a third image taken from the second pose, but at a time subsequent to the time at which the second image is taken, for purposes of measuring the distance dye within the blood vessel has moved and calculating a velocity based on the interval between the times the second and third images where taken.

Referring now to FIGS. 8, 9 and 10, the velocity of objects are measurable using registered fluoroscopic images and the techniques previously described for measuring distances. For example, the velocity with which radio-opaque dye flows through a blood vessel can be determined by marking the positions of the dye in two images taken at different times, calculating the distance between the marked positions, and calculating the velocity based on the time interval between the two images using the well known formula of the distance divided by the change in time. With the velocity, an estimate of the volumetric blood flow rate based on measured or a prior knowledge of the diameter of the blood vessel can be made. Two different approaches can be taken to measuring the distance of a moving object. In the first method, images are captured from the fluoroscope in at least two different poses and registered to a common coordinate system in order to provide the capability of specifying a point in three-dimensional space in each of a set of two-dimensional images taken of a simple pose. In the second approach, where the blood vessel, and thus the trajectory of the moving object, is relatively straight and lies within the plane of the image, such that there is no foreshortening, the images can be taken from only one pose. In each method, the computer can capture images from the fluoroscope at regular intervals, typically up to as many as thirty times a second, such that the time intervals between the images is known.

FIG. 8 is used only in connection with the first method. In FIG. 8, a first image 802 is acquired of the blood vessel 803 in a first pose. Radio-opaque dye 801 is seen transversing the blood vessel. The image, which is shown in screen 800, is registered to a known coordinate frame. In the illustrated example, artifact 40 (FIG. 3) is positioned in the field of view of the fluoroscope, resulting in the appearance of dots 804 representing the shadow of fiducials 44. The positions of the shadows are used to register the image to a known coordinate frame in the manner previously described.

In FIG. 9, the fluoroscope has been repositioned in order to capture images of the blood vessel in a second pose. Screen 900 displays a second image 902, which has been taken at a time subsequent to the first image 802 (FIG. 8). Dots 904, which are projections of the fiducials 44 of artifact 40 (FIG. 3), are used to register image 902 to the known coordinate frame in the manner previously described. Once the registration transform is obtained, it can be used to register all other images taken of this second pose. The position of the crest of the boundary of radio-opaque dye 801 within blood vessel 803 is marked with dot 906. This dot defines a line of sight in image 802 of FIG. 8. This line of sight is indicated by dashed line 806 in first image 802. Because the first and second images are now registered, the three-dimensional position of the crest of the dye is specified by marking with dot 808 where, along the line of sight 806 in the first image 802, the middle of the blood vessel is located. Dot 808 and dot 906 are thus constrained to the same three-dimensional point. Also, although not shown, lines approximately identifying the axis of the vessel can be drawn on the first and second images so that the position of the boundary of the dye can always be taken with respect to the center of the vessel.

A third image 1002, displayed in screen 1000 of FIG. 10, is taken at a subsequent time, such that the time interval between the second and third images is known. The position of the crest of the dye boundary is marked by dot 1004. Dot 1004 defines a line of sight in first image 802 of FIG. 8, which is represented by dashed line 810. The point at which the line of sight intersects with the middle of the blood vessel is marked with dot 812. Dots 812 and 1004 are therefore constrained to a single point in the three-dimensional coordinate system to which the images 802, 902 and 1002 are registered.

In response to activation of button 320, the computer then calculates distance between the marked positions of the dye. This distance is represented by line 1006. The result is provided in output field 322. Additional images can be taken to show the progression of the dye, with the position of the dye in each image indicated. Since the time each image was captured, relative to the other, is known, the velocity of the dye can be determined. Because the velocity of the dye is approximately the same as its carrier, the velocity of the blood flow is thus also known.

Furthermore, as indicated by dialog box 910, the computer, using well known equations, can estimate the volume of the blood vessel using the diameter and the velocity. The diameter of the blood vessel can be measured, in the manner previously described, or using estimate of the diameter that is already known. Activating button 908 causes the flow rate to be calculated and displayed in the dialog box 910. Activating button 912 causes the dialog box to be displayed. Although not illustrated, successive position measurements of the dye boundary, combined with the time intervals with which they were made, permits calculation of the acceleration of the blood flow velocity and rates.

In the second method, if the observed portion of the trajectory of the observed object is fairly straight and generally falls within the plane of the image, velocity along the path of movement of the object being measured can be determined using multiple images taken only of a single pose. A second position, which would otherwise be used to constrain the specification of the position to dye boundary in images taken from the first position, may not be necessary in this situation, especially if the scale of the image can be determined from a feature shown in the image. This second method is the same as described in connection with FIGS. 9 and 10, except that an image from a second position of the fluoroscope is not used. A priori knowledge of the dimension of an anatomical feature or other object within or close to the plane of the trajectory of the object, for example that defined by the blood vessel, permits deduction of a scale with which to determine actual distances. For example, knowledge of the actual physical dimensions of a stent that has been previously placed in the blood vessel, or of the typical diameter or length of the blood vessel being observed, can be used to create the scale with which to measure distances. Once the scale is specified, the computer can be used to determine actual distances based on marking the progress of the dye or other object. This second method will likely be less precise than the first method described above, and its usefulness is limited to particular situations.

As mentioned, both methods can also be adapted to be used to measure velocities and accelerations of other objects visible in fluoroscopic images, as well as to determine acceleration of an object.

Furthermore, certain methods and apparatus described above in connection with FIGS. 1-10 could be adapted to be used with or applied to other types of two-dimensional images, although they have particular advantage when used with fluoroscopic images.

The invention has been described in detail with reference to a certain preferred embodiments. Modifications may be made to the disclosed embodiments without departing from the scope of the invention as defined by the following claims.

The invention claimed is:

1. A computer-assisted method for determining a dimension of an anatomical feature using two or more fluoroscopic images, the method comprising:
    displaying a first fluoroscopic image taken of an anatomical feature taken from a first pose, the first image being registered to a common three-dimensional coordinate system;
    receiving indication of position of at least a first point and a second point within first image corresponding respectively to at least two anatomical landmarks shown within first image;
    displaying a second fluoroscopic image taken of the anatomical feature from a second angle, the second image being registered to the known three-dimensional coordinate system;
    indicating with reference to the second image where the anatomical landmarks lie along each of two lines of sight defined by the first and second points within the three-dimensional coordinate system; and
    determining a distance of a line specified by the first and second points.

2. The method of claim 1, further comprising:
    placing within the field of view of each fluoroscopic image a plurality of fiducials having known positions with respect to each other;
    receiving an input to identify two-dimensional coordinates of each of the plurality of fiducials displayed on each of the images; and
    registering the images by creating a geometric model having parameters, said model projecting three-dimensional coordinates of the plurality of fiducials into the identified coordinates of the fiducials on the images, and numerically optimizing the parameters of the geometric model such that the projections of the known three-dimensional coordinates of the fiducials best fit the identified two-dimensional coordinates in each of the images.

3. The method of claim 1 wherein the lines of sight are indicated on the second image by lines drawn on the second image.

4. A surgical planning system comprising:
    a fluoroscopic imaging device;
    at least one monitor for displaying fluoroscopic images; and
    a computer programmed to perform the method of claim 1.

5. An apparatus for determining a dimension of an anatomical feature using two or more fluoroscopic images, comprising:
    means for displaying a first fluoroscopic image taken of an anatomical feature taken from a first pose, the first image being registered to a common three-dimensional coordinate system;
    means for receiving indication of position of at least a first point and a second point within first image corresponding respectively to at least two anatomical landmarks shown within first image;
    means for displaying a second fluoroscopic image taken of the anatomical feature from a second angle, the second image being registered to the known three-dimensional coordinate system;
    means for indicating with reference to the second image where the anatomical landmarks lie along each of two lines of sight defined by the first and second points within the three-dimensional coordinate system; and
    means for determining distance of a line specified by the first and second points.

6. A non-transitory computer readable storage medium on which is recorded program instructions that, when read and executed by a computer, cause the computer to undertake the following steps:
    displaying a first fluoroscopic image taken of an anatomical feature taken from a first pose, the first image being registered to a common three-dimensional coordinate system;
    receiving indication of position of at least a first point and a second point within first image corresponding respectively to at least two anatomical landmarks shown within first image;
    displaying a second fluoroscopic image taken of the anatomical feature from a second angle, the second image being registered to the known three-dimensional coordinate system;
    indicating with reference to the second image where the anatomical landmarks lie along each of two lines of sight defined by the first and second points within the three-dimensional coordinate system; and
    determining distance of a line specified by the first and second points.

* * * * *